(12) United States Patent
Brookins

(10) Patent No.: US 11,400,470 B1
(45) Date of Patent: Aug. 2, 2022

(54) PORTABLE MIST BLOWER SYSTEM

(71) Applicant: ZAP MOSQUITO SOLUTIONS INC., Miami, FL (US)

(72) Inventor: Keith Donald Brookins, Miami, FL (US)

(73) Assignee: ZAP MOSQUITO SOLUTIONS INC., Miami, FL (US)

( * ) Notice: Subject to any disclaimer, the term of this patent is extended or adjusted under 35 U.S.C. 154(b) by 0 days.

(21) Appl. No.: 17/696,250

(22) Filed: Mar. 16, 2022

(51) Int. Cl.
*B05B 7/24* (2006.01)
*B05B 11/00* (2006.01)

(52) U.S. Cl.
CPC .......... *B05B 7/2408* (2013.01); *B05B 7/2416* (2013.01); *B05B 7/2424* (2013.01); *B05B 11/3087* (2013.01)

(58) Field of Classification Search
CPC ... B05B 7/2416; B05B 7/2408; B05B 7/2424; B05B 11/3087
USPC .................. 261/76, 115, 119.1, 111, 98, 99; 222/190; 239/77, 86, 412, 280
See application file for complete search history.

(56) References Cited

U.S. PATENT DOCUMENTS

| | | | | |
|---|---|---|---|---|
| 4,992,206 A | * | 2/1991 | Waldrop | B05B 7/10 261/78.2 |
| 5,248,448 A | * | 9/1993 | Waldron | B05B 7/10 261/78.2 |
| 7,878,418 B2 | * | 2/2011 | Sevy | B05B 7/2416 128/200.18 |
| 10,028,497 B1 | | 7/2018 | Brookins | |
| 10,799,838 B1 | | 10/2020 | Brookins | |
| 10,799,839 B1 | | 10/2020 | Brookins | |
| 2007/0278326 A1 | * | 12/2007 | Wu | H01M 50/209 239/332 |
| 2010/0072300 A1 | * | 3/2010 | Miller | B05B 9/0861 239/332 |
| 2012/0319309 A1 | | 12/2012 | Sorola et al. | |

* cited by examiner

*Primary Examiner* — Lien M Ngo
(74) *Attorney, Agent, or Firm* — Albert Bordas, P.A.

(57) ABSTRACT

A portable mist blower system, which has a housing assembly, a tank assembly, a handle assembly, a battery assembly, a pump motor assembly, a blower panel assembly, a manifold assembly, a blower assembly, and a solenoid assembly. The housing assembly has a front panel, a rear panel, a top panel, a bottom panel, and lateral panels. The tank assembly is secured to the top panel and trapped by the front panel, the battery assembly is secured to the top panel, the handle assembly is mounted onto the top panel, the pump motor assembly is secured to the rear panel, the blower panel assembly is mounted onto the front panel, the manifold assembly is connected to the blower panel assembly, and the blower assembly and the solenoid assembly are mounted onto the bottom panel.

20 Claims, 7 Drawing Sheets

PORTABLE MIST BLOWER SYSTEM

BACKGROUND OF THE INVENTION

Field of the Invention

The present invention relates to misting systems, and more particularly, to portable mist blower systems.

Description of the Related Art

Applicant believes that one of the closest references corresponds to Applicant's own U.S. Pat. No. 10,028,497 B1 issued to Keith Donald Brookins on Jul. 24, 2018 for Misting system. However, it differs from the present invention because Brookins teaches a misting system having an external compartment, an interior housing, a container housing, an electrical compartment, a lid assembly, and at least one outlet. The external compartment has a top face with a hole, a cavity, and an electrical cover panel. The interior housing has a top face with a hole, and lateral faces with a respective pivot hole. The container housing has lateral faces having pivoting protrusions, which are positioned onto each pivot hole of the interior housing lateral faces. The electrical compartment has a cover panel, a battery and a pump assembly. The lid assembly has a locking tab, a panel locking tab, a latching-limiter rod, and a spear. The electrical cover panel of the external compartment mounts onto the electrical compartment, and the cover panel of the electrical compartment mounts onto the external compartment. The lid assembly covers the external compartment and the electrical compartment.

Applicant believes that another reference corresponds to Applicant's own U.S. Pat. No. 10,799,838 B1 issued to Keith Donald Brookins on Oct. 13, 2020 for Multifunctional misting system. However, it differs from the present invention because Brookins teaches a multifunctional misting system having a housing assembly, a frame assembly, a recessed mist blower assembly, a valve assembly, a recess control panel assembly, a pump-motor assembly, a tank assembly, a puck assembly, and a handle assembly. The housing assembly has first and second flat panels, a front panel, a rear panel, a top panel, a bottom panel, and locking corners. The frame assembly has a solenoid side frame and a blower side frame, a mix solenoid, and a battery with a battery retainer. The recessed mist blower assembly has a blower and nozzles. The pump-motor assembly has a pump motor, a pump housing and a motor-battery bracket. The handle assembly is positioned onto the top panel of the housing assembly. The multifunctional misting system may operate as a mist blower.

Applicant believes that another reference corresponds to Applicant's own U.S. Pat. No. 10,799,839 B1 issued to Keith Donald Brookins on Oct. 13, 2020 for Multifunctional misting system. However, it differs from the present invention because Brookins teaches a multifunctional misting system having a housing assembly, a frame assembly, a mist blower assembly, a valve assembly, a recess control panel assembly, a pump-motor assembly, a tank assembly, and a handle assembly. The housing assembly has first and second flat panels, a front panel, a rear panel, a top panel, a bottom panel, and locking corners. The frame assembly has first and second frames, and a battery with a battery retainer. The mist blower assembly has a blower and nozzles. The pump-motor assembly is a motor attached to a pump. The motor has a motor-battery bracket fixed to the motor and a spacer. The handle assembly is positioned onto the top panel of the housing assembly. The multifunctional misting system may operate as a mist blower.

Applicant believes that another reference corresponds to U.S. Patent Publication No. 2012/0319309 A1 issued to Sorola; et al. on Dec. 20, 2012 for Rechargeable, Portable, Misting Beverage System. However, it differs from the present invention because Sorola; et al. teach a misting system utilizing spent ice that comprises a portable housing and an inner frame. The inner frame is secured inside the housing and is configured to receive ice and at least one of food and beverage. The inner frame has an outlet for passing the melted ice. A lid is provided for selectively enclosing the inner frame. The system includes a pump. The pump is inside the portable housing and is in communication with the inner frame outlet and an outlet of the portable housing. The pump is configured to pump melted ice from the inner frame to the outlet of the portable housing for use as mist.

Other patents describing the closest subject matter provide for a number of more or less complicated features that fail to solve the problem in an efficient and economical way. None of these patents suggest the novel features of the present invention.

SUMMARY OF THE INVENTION

The present invention is a portable mist blower system, comprising a housing assembly, a tank assembly, a handle assembly, a battery assembly, a pump motor assembly, a blower panel assembly, a manifold assembly, a blower assembly, and a solenoid assembly.

The housing assembly comprises a front panel, a rear panel, a top panel, a bottom panel, and lateral panels. The tank assembly is secured to the top panel and trapped by the front panel, the battery assembly is secured to the top panel, the handle assembly is mounted onto the top panel, the pump motor assembly is secured to the rear panel, the blower panel assembly is mounted onto the front panel, the manifold assembly is connected to the blower panel assembly, and the blower assembly and the solenoid assembly are mounted onto the bottom panel. The housing assembly houses the tank assembly, the battery assembly, the pump motor assembly, the manifold assembly, the blower assembly, and the solenoid assembly. The housing assembly further comprises corners, strap loops, air intake holes on the lateral panels, and feet on the bottom panel.

The front panel defines a blower panel cavity and comprises a mix switch hole, a power switch hole, and a charge port hole. The top panel comprises a tank neck hole and a fuse hole. The blower panel cavity receives the blower panel assembly, the mix switch hole receives a mix switch, the power switch hole receives a power switch, and the charge port hole receives a charge port.

The tank assembly comprises a tank body having a tank outlet, a tank upper section having a tank inlet to receive a mix tube, a tank neck, a tank strainer, a tank cap having a cap vent, a tank mounting flange, and a top flange. The tank neck passes through the tank neck hole and protrudes from the top panel to receive the tank cap.

The handle assembly comprises a handle body, a handle top, a handle grip, and a mist switch. The battery assembly comprises a battery, a control board, a fuse, a battery mounting bracket, and mounting screws. The fuse passes through the fuse hole and protrudes from the top panel.

The battery, the tank assembly, and the handle assembly are secured to the top panel with the mounting screws, whereby a leg of the battery mounting bracket and the top flange are fixed together to the top panel by the mounting screws.

The pump motor assembly comprises a pump, a pump output with a pump output tube, a pump input with a pump input tube, and a motor. The motor is secured to the rear panel with a motor bracket and a motor spacer is between the motor and the bottom panel.

The blower panel assembly comprises a blower panel, a bezel, a blower coupling shroud, a flapper, flapper pins, tee retainers, and nozzles. The manifold assembly comprises a tubing, tee adapters, a plug, and a manifold input, whereby the tee adapters are connected to the nozzles.

The blower assembly comprises a blower, a blower mounting structure, a blower outlet, a blower inlet, and first and second blower spacers. The blower coupling shroud fits into the blower, and the blower coupling shroud houses the flapper, which is secured by the flapper pins. The blower mounting structure is mounted onto the first and second blower spacers and the first and second blower spacers are secured to the bottom panel.

The solenoid assembly comprises a solenoid valve, first and second solenoid input connections, a solenoid output connector, and a main output tube. The pump input tube is connected from the tank outlet to the pump input. The main output tube is connected from the second input connector to the manifold input.

The solenoid assembly allows for a return fluid path for mixing and purge the air when the mix switch is depressed and drops the main output tube pressure upon the mist switch release allowing for a dripless operation.

It is therefore one of the main objects of the present invention to provide a portable mist blower system.

It is therefore one of the main objects of the present invention to provide a portable mist blower system, which has a blower.

It is another object of this invention to provide a portable mist blower system, which has a blower panel.

It is another object of this invention to provide a portable mist blower system that supports stationary nozzles.

It is another object of this invention to provide a portable mist blower system that is self-contained with a rechargeable battery.

It is another object of this invention to provide a portable mist blower system having a compact design.

It is another object of this invention to provide a portable mist blower system that has quiet operation avoiding noise ordinances being placed on blower type sprayers and the need to wear earmuff protection.

It is another object of this invention to provide a portable mist blower system, which has a solenoid assembly that provides purging, mixing, and anti-drip.

It is another object of this invention to provide a portable mist blower system designed to be light weight.

It is another object of this invention to provide a portable mist blower system that is volumetrically efficient for carrying, transporting, and storage.

It is another object of this invention to provide a portable mist blower system that can be readily assembled and disassembled without the need of any special tools.

It is another object of this invention to provide a portable mist blower system, which is of a durable and reliable construction.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE INVENTION

Figure 1A:
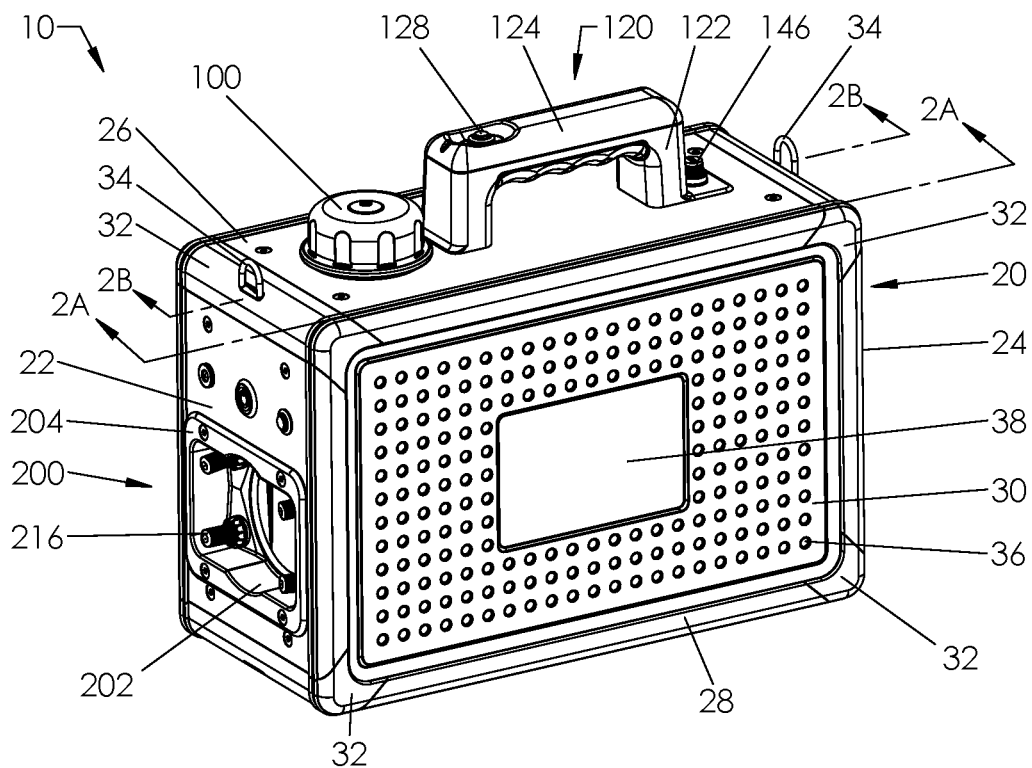
FIG. 1A is a front isometric view of the present invention.

Referring now to the drawings, the present invention is a portable mist blower system and is generally referred to with numeral 10. It can be observed that it basically includes housing assembly 20, tank assembly 90, handle assembly 120, battery assembly 140, pump motor assembly 160, blower panel assembly 200, manifold assembly 220, blower assembly 230, and solenoid assembly 250.

Figure 1B:
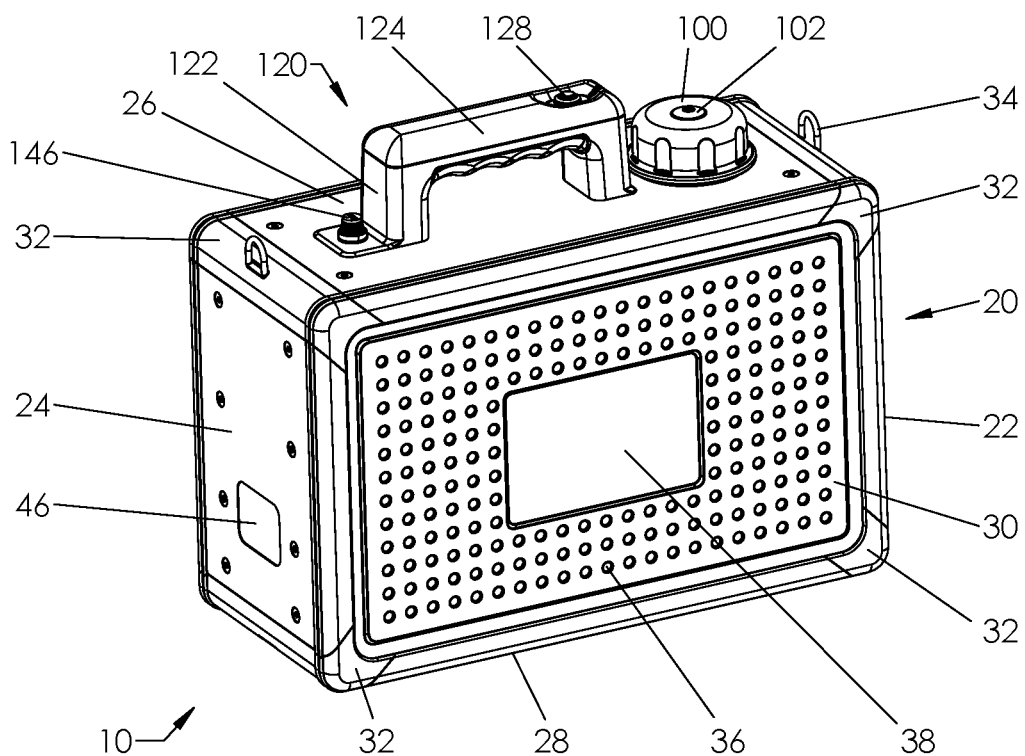
FIG. 1B is a rear isometric view of the present invention.

As seen in FIGS. 1A and 1B, housing assembly 20 comprises front panel 22, rear panel 24, top panel 26, bottom panel 28, and lateral panels 30. Housing assembly 20 further comprises corners 32. Corners 32 connect front panel 22 and rear panel 24 to top panel 26 and bottom panel 28. Corners 32 joined to top panel 26 comprise first and second strap loops 34. Lateral panels 30 comprise air intake holes 36. Air intake holes 36 are designed to prevent rodent and/or insect intrusion while providing adequate air intake. In a preferred embodiment, lateral panels 30 comprise solid area 38 approximately at a center, and rear panel 24 comprises info area 46. Handle assembly 120 is mounted onto top panel 26. Blower panel assembly 200 is mounted onto front panel 22.

Present invention 10 is a portable mist blower system for solutions. Such solutions can be, but are not limited to, anti-pathogen agents, insect controls whether adult or pre-emergent including mosquitoes, bed bugs, lice, and mites. Solutions further include insect repellents, extermination treatments, plant health fertilizers, insecticides, fungicides, surfactants for drought resistance in public health applications, mold mitigation, sunscreen, sanitation products such as sanitizers and anti-pathogens, and odor controllers such as deodorizers and fragrances.

As seen in FIGS. 2A and 2B, housing assembly 20 houses tank assembly 90, battery assembly 140, pump motor assembly 160, manifold assembly 220, seen in FIG. 3, blower assembly 230, and solenoid assembly 250. Pump input tube 170 is connected from tank outlet 106 to pump input 166. Main output tube 258 is connected from solenoid input connection 255 to manifold input 228, seen in FIG. 6. Solenoid valve 252 discharges main output tube 258 pressure upon mister deactivation dropping line pressure for anti-drip.

Figure 3:
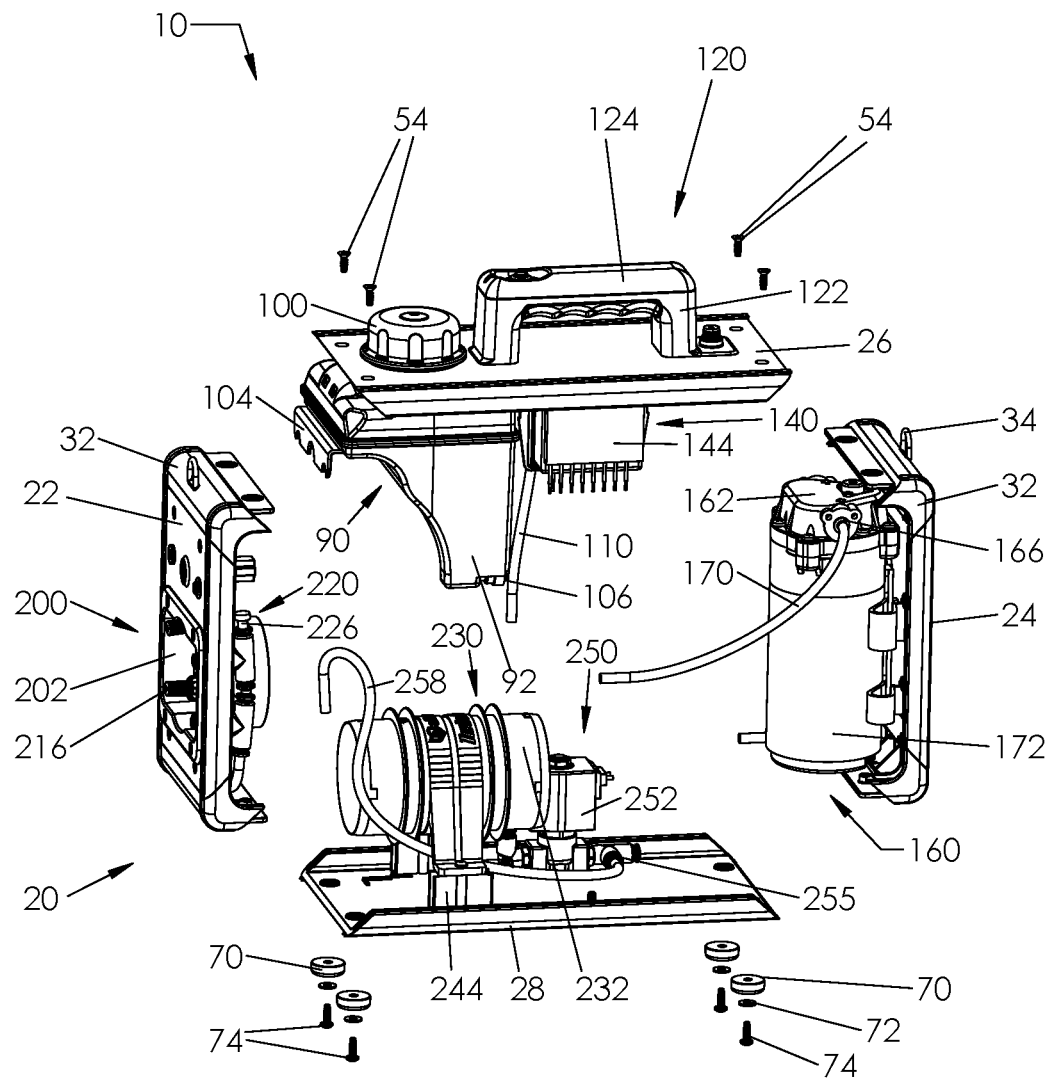
FIG. 3 is a partial exploded view of the present invention.

As seen in FIG. 3, tank assembly 90 and battery assembly 140 are secured to top panel 26. Pump motor assembly 160 is secured to rear panel 24, and blower assembly 230 and solenoid assembly 250 are mounted onto bottom panel 28. Manifold assembly 220 is connected to blower panel assembly 200. Housing assembly 20 further comprises feet 70. Feet 70 are fixed to bottom panel 28 with feet washers 72 and feet screws 74. Feet screws 74 also work as corner screws, since feet screws 74 secure corresponding corners 32 to bottom panel 28. Corner screws 54 secure corners 32 on front panel 22, rear panel 24, and top panel 26.

Figure 2A:
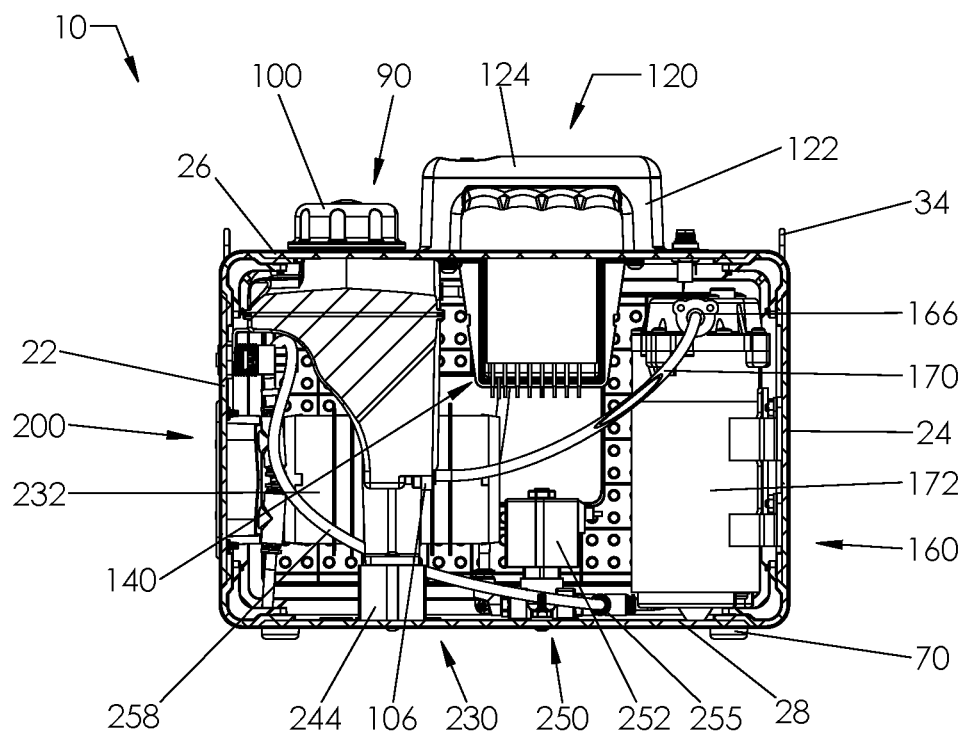
FIG. 2A is a cut view taken along lines 2A-2A from FIG. 1A.
Figure 4:
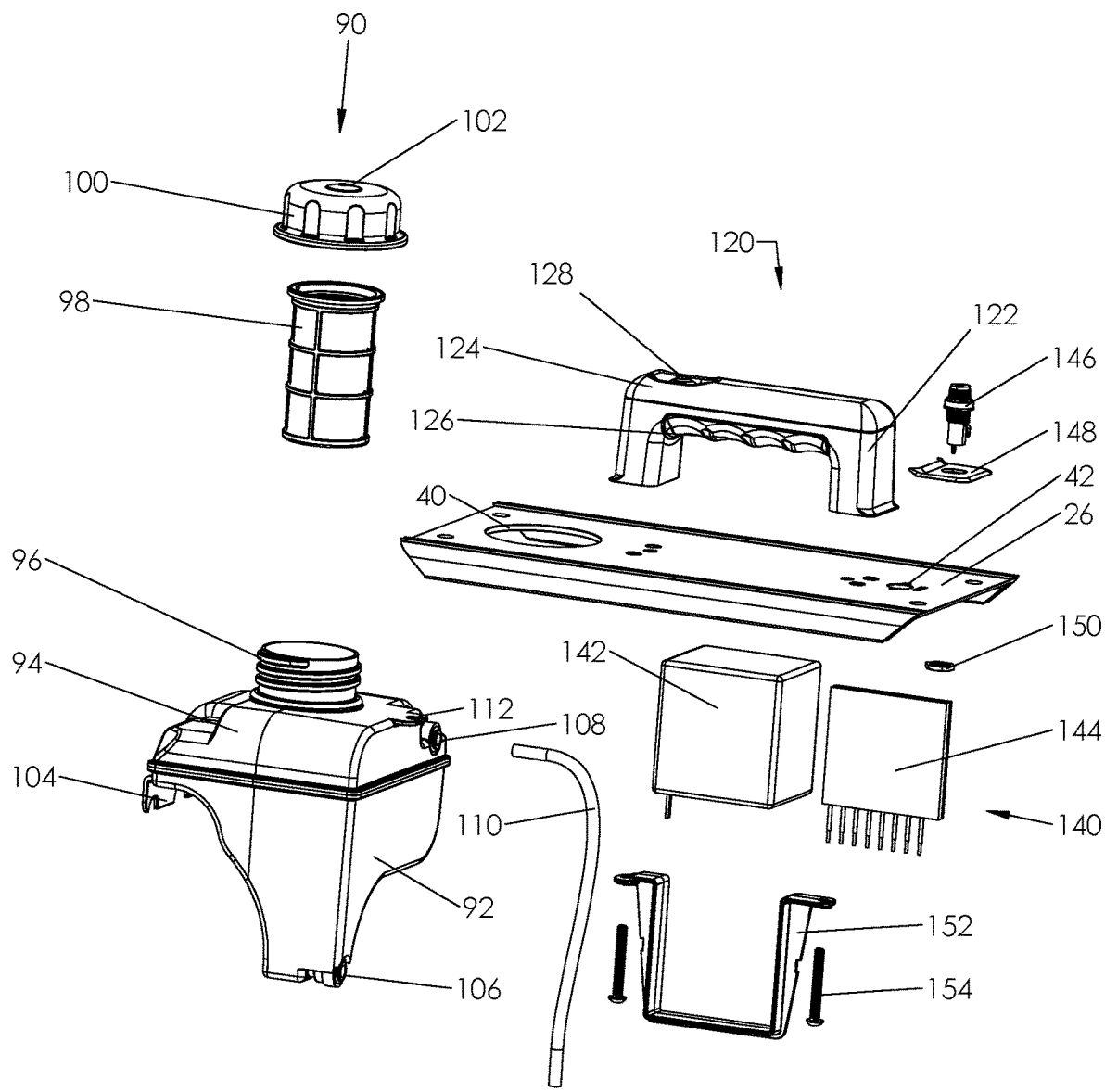
FIG. 4 is a partial exploded view of a top section of the present invention, which has a handle assembly, a tank assembly, and a battery assembly.

As seen in FIG. 4, top panel 26 comprises tank neck hole 40 and fuse hole 42. Tank assembly 90 comprises tank body 92, tank upper section 94, tank neck 96, tank strainer 98, tank cap 100 having cap vent 102, tank mounting flange 104, and top flange 112. Tank upper section 94 comprises tank inlet 108, which receives mix tube 110. Tank body 92 comprise tank outlet 106. Tank assembly 90 is secured on top panel 26 and trapped by front panel 22, seen in FIG. 2A. Tank assembly 90 rests on mix switch 58, power switch 60, and charge port 62, seen in FIG. 6, through tank mounting flange 104, while tank neck 96 passes through tank neck hole 40 protruding from top panel 26 to receive tank cap 100. Tank assembly 90 is secured to top panel 26 through top flange 112 with bracket mounting screws 154. Handle assembly 120 is fixed onto top panel 26. Handle assembly 120 comprises handle body 122, handle top 124, handle grip 126, and mist switch 128.

Battery assembly 140 comprises battery 142, control board 144, fuse 146, and battery mounting bracket 152. Fuse 146 passes through fuse hole 42 and protrudes from top panel 26. Fuse spacer 148 is positioned between top panel 26 and fuse 146. Fuse 146 is secured by fuse nut 150. Battery 142 comprises a battery management system. Battery 142 is charged through charge port 62, seen in FIG. 4, with a charger, not seen. Battery 142 is secured to top panel 26 by battery mounting bracket 152 and battery mounting screws 154. Battery mounting screws 154 secure tank assembly 90, battery 142, and handle assembly 120 to top panel 26. A leg of battery mounting bracket 152 and top flange 112 are fixed together to top panel 26 by battery mounting screw 154, which passes through top panel 26 to receive and secure handle body 122.

Figure 2B:
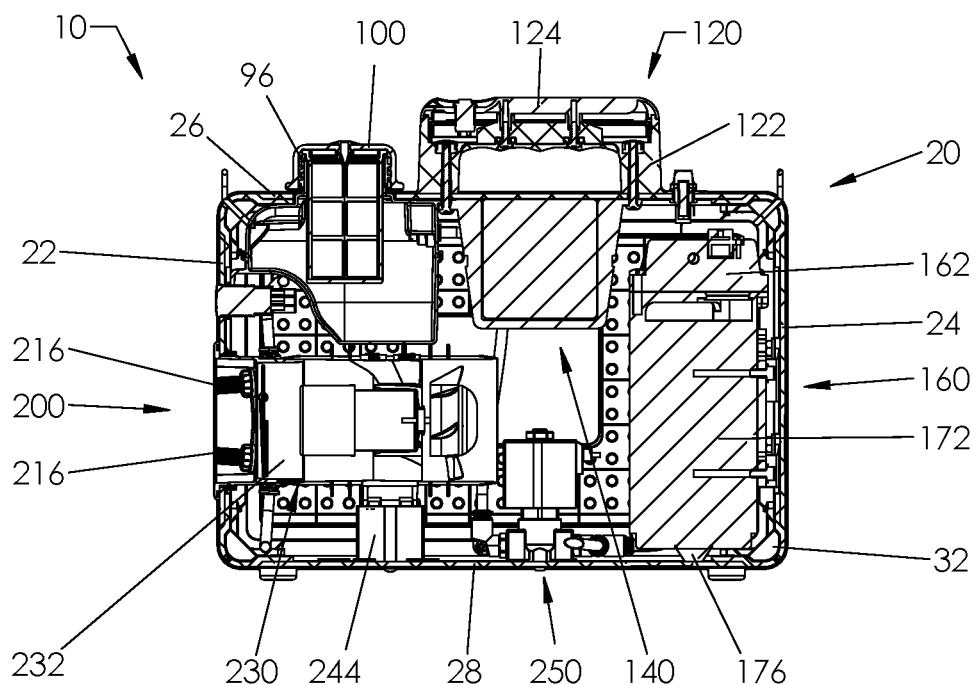
FIG. 2B is a cut view taken along lines 2B-2B from FIG. 1A.
Figure 5:
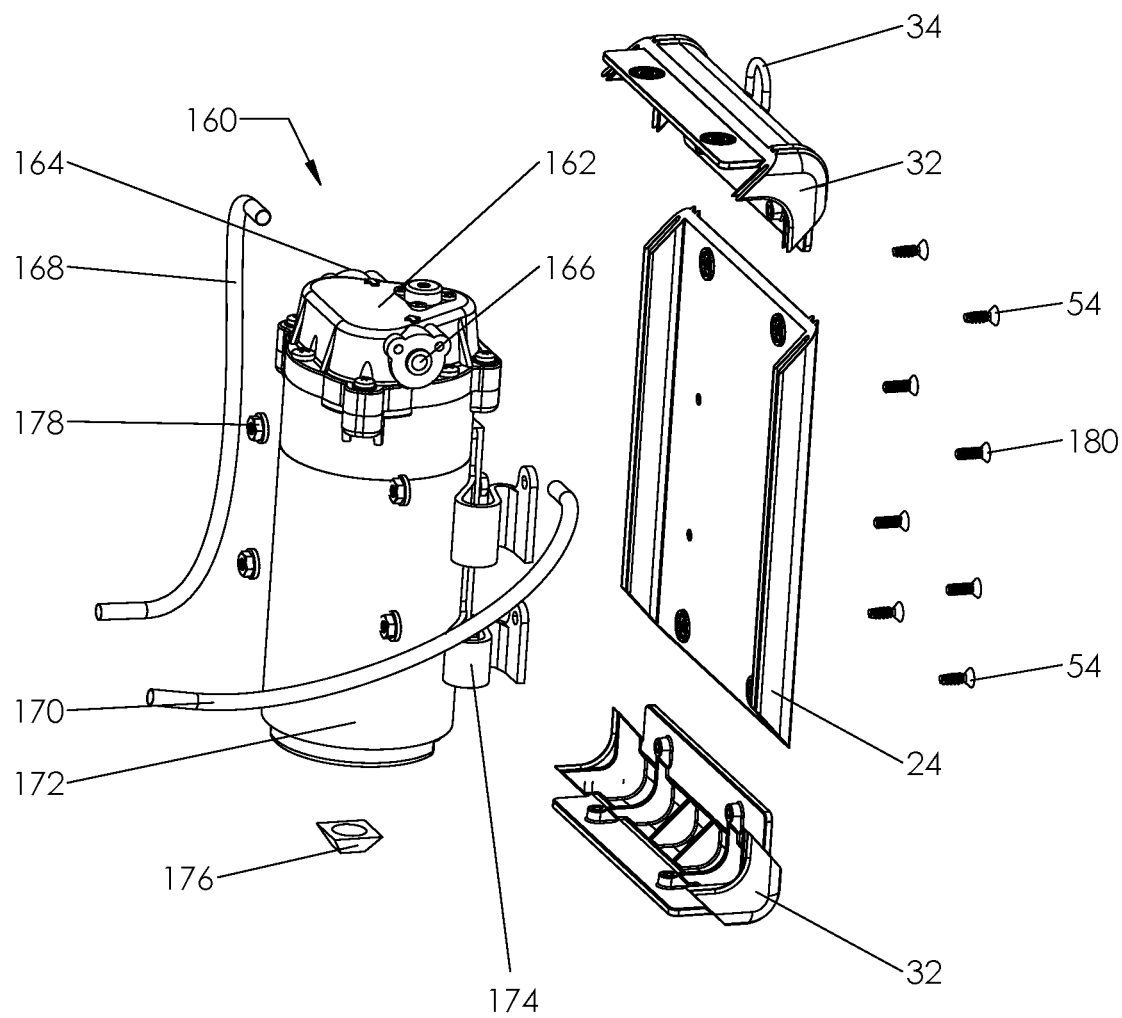
FIG. 5 is a partial exploded view of the rear section of the present invention having a pump motor assembly.

As seen in FIG. 5, pump motor assembly 160 comprises pump 162, pump output 164 to connect pump output tube 168, pump input 166 to connect pump input tube 170, and motor 172. Motor 172 is secured to rear panel 24 by motor bracket 174 with pump-motor mount screws 180 secured by pump-motor mount nuts 178. Motor spacer 176 is between motor 172 and bottom panel 28, as seen in FIG. 2B.

Figure 6:
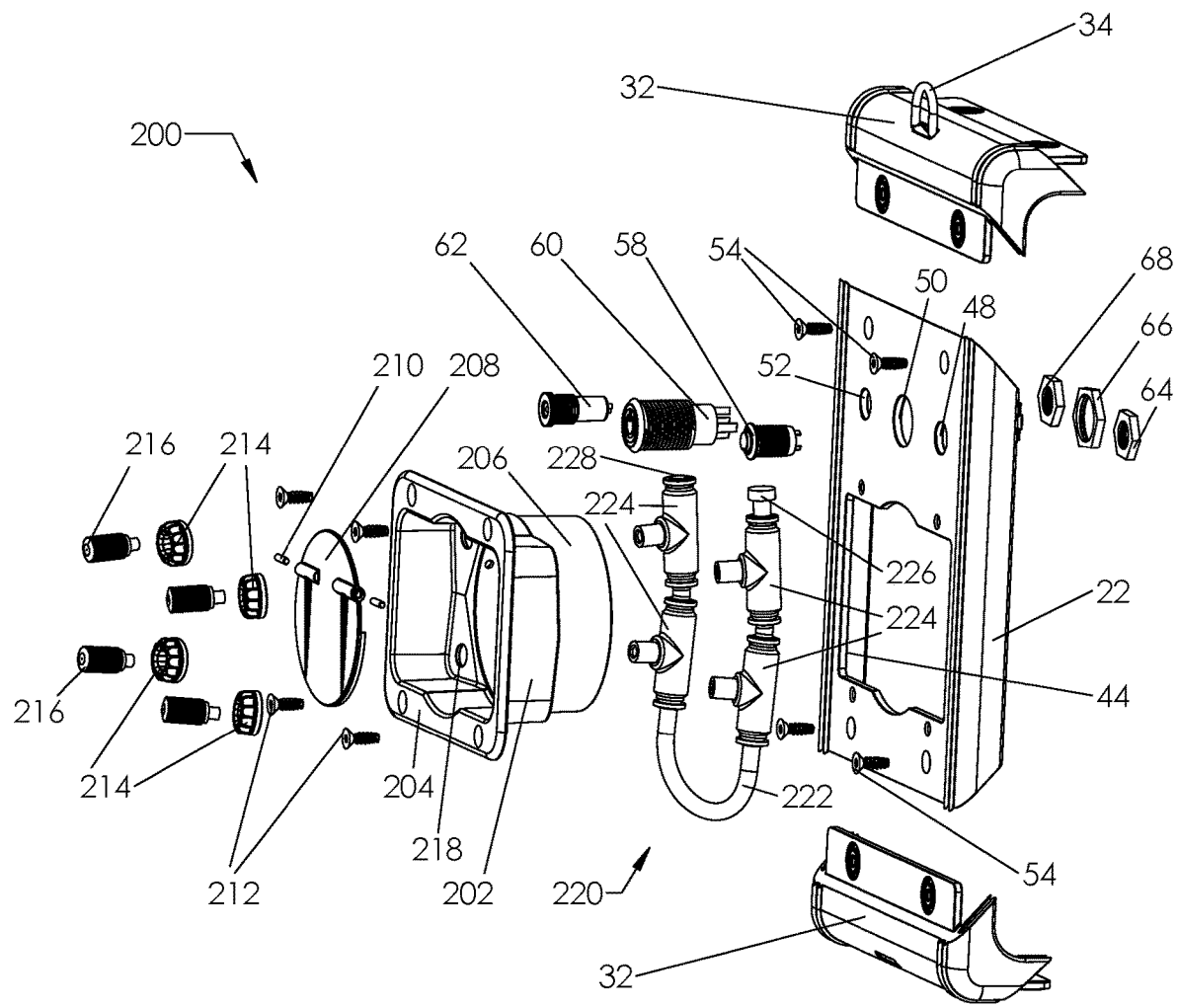
FIG. 6 is an exploded view of the front section of the present invention having a blower panel assembly.

As seen in FIG. 6, front panel 22 defines blower panel cavity 44, mix switch hole 48, power switch hole 50, and charge port hole 52. Mix switch hole 48 receives mix switch 58, power switch hole 50 receives power switch 60, and charge port hole 52 receives charge port 62. Mix switch 58, power switch 60, and charge port 62 are secured to front panel 22 with mix switch nut 64, power switch nut 66, and charge port nut 68, respectively. Mix switch 58 allows solenoid assembly 250, seen in FIG. 3, to purge the pump of air. Depressing mix switch 58 allows for in-tank mixing or re-mixing. Blower panel cavity 44 receives blower panel assembly 200. Blower panel assembly 200 comprises blower panel 202, bezel 204, blower coupling shroud 206, flapper 208, flapper pins 210, tee retainers 214, and nozzles 216. In a preferred embodiment, there are four tee retainers 214 and four nozzles 216. Bezel 204 is secured to front panel 22 with blower panel screws 212. Blower coupling shroud 206 houses flapper 208, which is secured by flapper pins 210.

Manifold assembly 220 comprises tubing 222, tee adapters 224, and plug 226. Blower panel 202 comprises tee adapter holes 218 to receive respective tee adapters 224. Tee adapters 224 are connected to respective nozzle 216.

Figure 7:
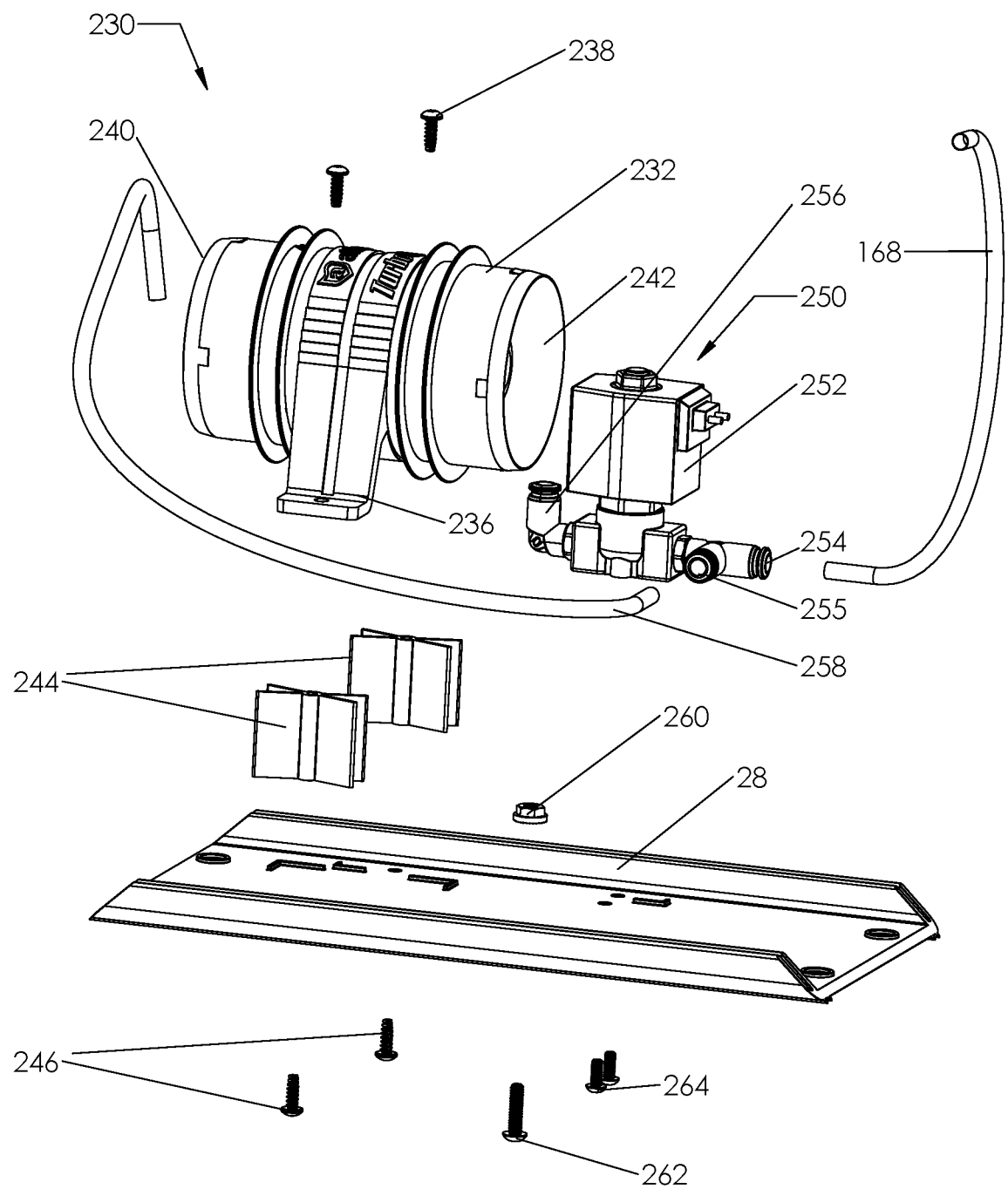
FIG. 7 is a partial exploded view of the bottom section of the present invention having a blower assembly and a solenoid assembly.

As seen in FIG. 7, blower assembly 230 comprises blower 232, blower mounting structure 236, blower outlet 240, blower inlet 242, and first and second blower spacers 244. Blower mounting structure 236 is mounted onto first and second blower spacers 244 and fixed with blower mounting screws 238. First and second blower spacers 244 are secured to bottom panel 28 by blower spacer screws 246. Blower assembly 230 is connected to blower panel assembly 200, seen in FIG. 6, whereby blower coupling shroud 206, seen in FIG. 6, fits into blower 232.

Solenoid assembly 250 comprises solenoid valve 252, solenoid input connections 254 and 255, solenoid output connector 256, and main output tube 258, which is connected to solenoid input connection 255. Solenoid assembly 250 is secured onto bottom panel 28 by solenoid mounting screws 264. Solenoid assembly 250 further comprises ground bus 262 and ground bus nut 260. Solenoid input connections 254 and 255 may act as an input or output depending if solenoid assembly 250 is on or off. Pump output tube 168 is connected from pump output 164, seen in FIG. 5, to solenoid input connection 254. When solenoid valve 252 is not being used, pump output tube 168 sources main output tube 258. Solenoid assembly 250 drops main output tube 258 pressure when misting stops upon mist switch 128, seen in FIG. 4, release allowing for dripless operation. Solenoid assembly 250 allows for a return fluid path for mixing when mix switch 58, seen in FIG. 6, is depressed. Solenoid assembly 250 purges the pump of air. This allows users to purge air from the pump motor assembly 160, seen in FIG. 3, so it reaches optimum pressure and by returning the purge fluid back to tank assembly 90, it prevents the alternative of misting out onto the ground.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A portable mist blower system, comprising:
A) a housing assembly comprising a front panel, a rear panel, a top panel, a bottom panel, and lateral panels;
B) a tank assembly secured to said top panel and trapped by said front panel;
C) a handle assembly mounted onto said top panel;
D) a battery assembly secured to said top panel;
E) a pump motor assembly secured to said rear panel;
F) a blower panel assembly mounted onto said front panel;
G) a manifold assembly connected to said blower panel assembly;
H) a blower assembly mounted onto said bottom panel; and
I) a solenoid assembly mounted onto said bottom panel, whereby said housing assembly houses said tank assembly, said battery assembly, said pump motor assembly, said manifold assembly, said blower assembly, and said solenoid assembly.

2. The portable mist blower system set forth in claim 1, wherein said housing assembly further comprises corners, strap loops, air intake holes on said lateral panels, and feet on said bottom panel.

3. The portable mist blower system set forth in claim 1, wherein said front panel defines a blower panel cavity, said front panel comprises a mix switch hole, a power switch hole, and a charge port hole, and said top panel comprises a tank neck hole and a fuse hole.

4. The portable mist blower system set forth in claim 3, wherein said blower panel cavity receives said blower panel assembly, said mix switch hole receives a mix switch, said power switch hole receives a power switch, and said charge port hole receives a charge port.

5. The portable mist blower system set forth in claim 4, wherein said tank assembly comprises a tank body having a tank outlet, a tank upper section having a tank inlet to receive a mix tube, a tank neck, a tank strainer, a tank cap having a cap vent, a tank mounting flange, and a top flange.

6. The portable mist blower system set forth in claim 5, wherein said tank neck passes through said tank neck hole and protrudes from said top panel to receive said tank cap.

7. The portable mist blower system set forth in claim 5, wherein said handle assembly comprises a handle body, a handle top, a handle grip, and a mist switch.

8. The portable mist blower system set forth in claim 3, wherein said battery assembly comprises a battery, a control board, a fuse, a battery mounting bracket, and battery mounting screws.

9. The portable mist blower system set forth in claim 8, wherein said fuse passes through said fuse hole and protrudes from said top panel.

10. The portable mist blower system set forth in claim 8, wherein said battery, said tank assembly, and said handle assembly are secured to said top panel with said battery mounting screws, whereby a leg of said battery mounting bracket and said top flange are fixed together to said top panel by said battery mounting screws.

11. The portable mist blower system set forth in claim 7, wherein said pump motor assembly comprises a pump, a pump output with a pump output tube, a pump input with a pump input tube, and a motor.

12. The portable mist blower system set forth in claim 11, wherein said motor is secured to said rear panel with a motor bracket and a motor spacer is between said motor and said bottom panel.

13. The portable mist blower system set forth in claim 11, wherein said blower panel assembly comprises a blower panel, a bezel, a blower coupling shroud, a flapper, flapper pins, tee retainers, and nozzles.

14. The portable mist blower system set forth in claim 13, wherein said manifold assembly comprises a tubing, tee adapters, a plug, and a manifold input, whereby said tee adapters are connected to said nozzles.

15. The portable mist blower system set forth in claim 13, wherein said blower assembly comprises a blower, a blower mounting structure, a blower outlet, a blower inlet, and first and second blower spacers.

16. The portable mist blower system set forth in claim 15, wherein said blower coupling shroud fits into said blower, and said blower coupling shroud houses said flapper, which is secured by said flapper pins.

17. The portable mist blower system set forth in claim 15, wherein said blower mounting structure is mounted onto said first and second blower spacers and said first and second blower spacers are secured to said bottom panel.

18. The portable mist blower system set forth in claim 14, wherein said solenoid assembly comprises a solenoid valve, first and second solenoid input connections, a solenoid output connector, and a main output tube.

19. The portable mist blower system set forth in claim 18, wherein said pump input tube is connected from said tank outlet to said pump input and said main output tube is connected from said second input connector to said manifold input.

20. The portable mist blower system set forth in claim 18, wherein said solenoid assembly allows for a return fluid path for mixing and purging air when said mix switch is depressed and drops said main output tube pressure upon said mist switch release, allowing for a dripless operation.

* * * * *